United States Patent
Barde et al.

(10) Patent No.: US 11,165,271 B2
(45) Date of Patent: Nov. 2, 2021

(54) CONTROL DEVICE AND METHOD FOR CHARGING A NON-AQUEOUS RECHARGEABLE METAL-AIR BATTERY

(71) Applicant: TOYOTA MOTOR EUROPE, Brussels (BE)

(72) Inventors: Fanny Barde, Brussels (BE); Keita Komiyama, Brussels (BE)

(73) Assignee: TOYOTA MOTOR EUROPE, Brussels (BE)

( * ) Notice: Subject to any disclaimer, the term of this patent is extended or adjusted under 35 U.S.C. 154(b) by 159 days.

(21) Appl. No.: 16/312,218

(22) PCT Filed: Aug. 19, 2016

(86) PCT No.: PCT/EP2016/069713
§ 371 (c)(1),
(2) Date: Dec. 20, 2018

(87) PCT Pub. No.: WO2018/033217
PCT Pub. Date: Feb. 22, 2018

(65) Prior Publication Data
US 2019/0237835 A1 Aug. 1, 2019

(51) Int. Cl.
*H02J 7/00* (2006.01)
*H01M 10/48* (2006.01)
(Continued)

(52) U.S. Cl.
CPC .......... *H02J 7/00719* (2020.01); *G01N 21/00* (2013.01); *G01N 33/004* (2013.01);
(Continued)

(58) Field of Classification Search
CPC .................................................. H02J 7/00719
(Continued)

(56) References Cited

U.S. PATENT DOCUMENTS

2009/0239132 A1* 9/2009 Johnson .............. H01M 8/0668
429/61
2012/0223680 A1* 9/2012 Ryu ...................... H01M 10/44
320/137
(Continued)

FOREIGN PATENT DOCUMENTS

JP 2012-216310 A 11/2012

OTHER PUBLICATIONS

Nov. 9, 2016 International Search Report issued in International Patent Application No. PCT/EP2016/069713.
(Continued)

*Primary Examiner* — Eric D Lee
(74) *Attorney, Agent, or Firm* — Oliff PLC

(57) ABSTRACT

A control device for controlling charging of a non-aqueous metal air battery, the control device being configured to: determine a $CO_2$ concentration ($C_x$) and an increase rate ($RCO_2$) of $CO_2$ concentration in the battery, charge the battery in case both the $CO_2$ concentration ($C_x$) before starting charging exceeds a predetermined $CO_2$ threshold ($C_T$) and the increase rate of the $CO_2$ concentration ($RCO_2$) during charging is below a predetermined threshold value ($\Delta C_T/\Delta Ah_T$, $\Delta C_T/\Delta t$), and stop charging when the increase rate ($RCO_2$) exceeds the predetermined threshold value ($\Delta C_T/\Delta Ah_T$, $\Delta C_T/\Delta t$). Also, a corresponding method of controlling charging of a rechargeable battery.

19 Claims, 4 Drawing Sheets

(51) Int. Cl.
  *G01N 21/00* (2006.01)
  *H01M 10/44* (2006.01)
  *H01M 12/08* (2006.01)
  *G01N 33/00* (2006.01)
  *H01M 12/02* (2006.01)
  *H01M 4/38* (2006.01)
  *B60L 53/60* (2019.01)
  *B60L 50/64* (2019.01)
  *B60K 6/28* (2007.10)

(52) U.S. Cl.
  CPC ....... *H01M 10/441* (2013.01); *H01M 10/482* (2013.01); *H01M 12/02* (2013.01); *H01M 12/08* (2013.01); *B60K 6/28* (2013.01); *B60L 50/64* (2019.02); *B60L 53/60* (2019.02); *B60Y 2200/91* (2013.01); *B60Y 2200/92* (2013.01); *B60Y 2300/91* (2013.01); *B60Y 2400/112* (2013.01); *H01M 4/382* (2013.01); *H01M 2220/20* (2013.01); *Y02E 60/10* (2013.01)

(58) Field of Classification Search
  USPC .......................................................... 320/147
  See application file for complete search history.

(56) References Cited

U.S. PATENT DOCUMENTS

2012/0249080 A1  10/2012  Suto
2015/0024291 A1   1/2015  Ito et al.
2015/0303723 A1*  10/2015  Raghavan ................. H02J 7/00
                                                              320/107

OTHER PUBLICATIONS

Nov. 9, 2016 Written Opinion of the International Searching Authority issued in International Patent Application No. PCT/EP2016/069713.

* cited by examiner

CONTROL DEVICE AND METHOD FOR CHARGING A NON-AQUEOUS RECHARGEABLE METAL-AIR BATTERY

FIELD OF THE DISCLOSURE

The present disclosure is related to a control device for controlling charging of a metal air battery, in particular a non-aqueous rechargeable metal air battery, and also to a method of charging of a non-aqueous metal air battery.

BACKGROUND OF THE DISCLOSURE

Rechargeable batteries, also called secondary cells, have become increasingly important as energy storages, in particular for vehicles or stationary applications. Such vehicles may be hybrid vehicles comprising an internal combustion engine and one or more electric motors or purely electrically driven vehicles.

Recently, metal air batteries have become important due to advances in materials technology and an increasing demand for renewable energy sources. A battery may be realized by a single cell but typically it is designed as a battery pack, since it comprises an assembly (in series or parallel) of various modules, themselves composed of several cells.

A metal air battery is usually composed of a metal anode, a (non-aqueous) electrode and an air cathode, where $O_2$ is the main reactant. The air cathode is typically a Gaz Diffusion Electrode (denoted GDE). For example, it may be composed typically of Carbon or any other conductive materials (gold, nickel . . . ), a binder and sometimes a catalyst. The catalyst can be in a solid form and contained in the air cathode. The catalyst can also be a soluble catalyst which is dissolved in certain ratio in the electrolyte and acts as a redox mediator (e.g. Tetratiafulvalene (TTF) or Iodine). In both cases, it is expected from the catalysts that they will facilitate the decomposition of the ideal discharge product being typically $Li_2O_2$. This $Li_2O_2$ is supposed to be decomposed during the charge to form back $Li^+$ and $O_2$.

The cathode is usually a support for $O_2$ reaction. The ideal reaction should be as follows:

During discharge $O_2$ is consumed to form the ideal product $Li_2O_x$:$2 Li+x/2 O_2 \rightarrow Li_2O_x$. This reaction is actually taking place in several steps in which the first one is related to the formation of $O_2^-$ radicals as follows: $O_2+e^- \rightarrow O_2^-$.

During charge $O_2$ is released: $Li_2O_x \rightarrow 2 Li+x/2 O_2$.

Nevertheless, during electrochemical processes of the battery, it can happen that some side reactions take place (for example $O_2^-$ radicals react with the solvent molecules of the electrolyte and lead to the formation of side reactions products such as Lithium Carbonate ($Li_2CO_3$), Li formate, Lithium acetate, etc.). As a result, during the charging process it can happen that $CO_2$ gas is released. In such case, bad re-chargeability of the battery occurs and poor capacity retention is observed.

Accordingly, during charging of the battery as described above, it is possible that an unwanted product such as $CO_2$ gas is evolved instead of or in addition to the expected $O_2$ gas. This $CO_2$ is detrimental for the battery since it contributes to the degradation of the battery.

Furthermore, this $CO_2$ is an indication that the battery is overcharging and usually is linked with a strong increase of voltage which is an indication of an unsafe use of the battery.

US 2012/0249080 A1 teaches a system which avoids the formation of $H_2$ which is unsafe and detrimental for battery performances in the cathode of a metal air battery. The battery is a hybrid battery having a non-aqueous electrolyte at the anode side and an aqueous electrolyte at the cathode side.

JP2012-216310 A describes an aqueous metal air battery where electrolyte is typically based on a basis aqueous solution. A sensor for detecting $CO_2$ is provided. In case $CO_2$ is detected above the threshold value the battery charging stops.

However, since in such conventional art the threshold value is only set once initially, the battery cannot be charged after the degradation occurred if the concentration of $CO_2$ is already above the threshold value before the battery is charging. In other words, when the $CO_2$ concentration detected in the system is above a threshold value, the battery cannot be charged anymore.

SUMMARY OF THE DISCLOSURE

Currently, it remains desirable to provide a control device which provides a charging control function allowing an extended and anyway safe use of a metal air battery during its lifetime.

Therefore, according to embodiments of the present disclosure, a control device is provided for controlling charging of a non-aqueous metal air battery, the control device being configured to:

determine a $CO_2$ concentration and an increase rate of $CO_2$ concentration in the battery, charge the battery in case both the $CO_2$ concentration before starting charging exceeds a predetermined $CO_2$ threshold and the increase rate of the $CO_2$ concentration during charging is below a predetermined threshold value, and stop charging when the increase rate exceeds the predetermined threshold value.

By providing such a configuration it is possible to control charging in dependence on the increase rate of $CO_2$ concentration as a (first) criterion, beside the conventional (second) criterion related to the absolute $CO_2$ concentration detected in the system. The first criterion is related to the rate at which the $CO_2$ will be formed in the battery. This first criterion allows the battery to continue to be charged even if $CO_2$ release already occurred, i.e. the absolute $CO_2$ concentration detected in the system has already increased during lifetime of the battery.

Accordingly, even if $CO_2$ release already occurred being above the predetermined $CO_2$ threshold, the battery can still be charged. In such a case the predetermined threshold is not applicable anymore, since the $CO_2$ concentration in the battery exceeds said predetermined $CO_2$ threshold already before starting charging. Therefore the increase rate of $CO_2$ concentration in the battery during charging may be used to control charging.

In other words, the control device can judge whether or not the metal air battery can continue to be charged by detecting the concentration of $CO_2$ and the rate of increase of $CO_2$ concentration. By doing so, expected battery degradation can be prevented and as a result the lifetime of the battery can be extended. Further, the battery can be charged at best and accordingly increase the capacity of charge even in presence of a relatively small amount of $CO_2$ released.

Moreover, since $CO_2$ emission is an indication that the battery is overcharging and is usually related to a strong increase of voltage which is an indication of an unsafe use of the battery, the control device can provide a safer charging procedure by monitoring during charging both the $CO_2$ concentration and the increase rate of $CO_2$ concentration.

The predetermined threshold value may also be referred to as a predetermined increase rate threshold value or a predetermined relation threshold value.

The $CO_2$ concentration determined in the battery before starting charging and/or during charging may also be expressed as the total and/or absolute $CO_2$ concentration.

The control device may be further configured to:

charge the battery, in case the $CO_2$ concentration in the battery before starting charging does not exceed the predetermined $CO_2$ threshold, and in this case, stop charging when the $CO_2$ concentration in the battery during charging increases such that it exceeds the predetermined $CO_2$ threshold.

Accordingly, in case the battery is e.g. a relatively new battery having a relatively low $CO_2$ concentration below the predetermined $CO_2$ threshold, a conventional control mechanism can be applied which stops charging in case of a significant increase of the $CO_2$ concentration during charging.

Hence, the predetermined threshold value (i.e. the increase rate threshold value) desirably only becomes relevant as a trigger to stop charging, in case the $CO_2$ concentration in the battery before starting charging exceeds the predetermined $CO_2$ threshold. Otherwise the $CO_2$ threshold may be used as the trigger to stop charging.

The increase rate of $CO_2$ concentration may be a $CO_2$/capacity relation. Said $CO_2$/capacity relation may be in particular a relation between the increment of $CO_2$ concentration during a predetermined time interval and the increment of capacity of the battery during the predetermined time interval.

Accordingly, it is possible to use as a first criterion the development of the $CO_2$ concentration in view of capacity change during charging. It has been found that such a relation is a reliable criterion to determine whether charging may be continued or not without harming the battery or any unsafe use of the battery.

In other words, the control device may take into consideration the amount of $CO_2$ release (rate at which $CO_2$ is formed in the battery) versus the capacity increase and may monitor that it stays within a certain range.

Generally, a battery's capacity is the amount of electric charge it can deliver at a rated voltage. The capacity is measured in units such as amp-hour (A·h). Accordingly, the increase rate of capacity may be the current flowing into the battery during charging. The increase rate of capacity may be measured in units such as amp (A). The theoretical capacity of Li—$O_2$ battery generally results from the amount of Li metal present in the battery and the amount of $O_2$ delivered to the battery. While the first one is decided when the battery is built, the second one ($O_2$) can be infinite in practice since it depends on the amount of gas (air or $O_2$) made available to the battery. In practice the capacity is usually limited by the design of the cathode where some pores clogging may occur when too much $Li_2O_2$ is deposited. Hence, the amount of theoretical capacity of a Li—$O_2$ battery configuration can be found out by experience.

The control device may be further configured to stop charging, when the $CO_2$/capacity relation exceeds a predetermined $CO_2$/capacity relation threshold (i.e. the predetermined threshold value).

Accordingly, if the $CO_2$/capacity relation does not exceed the predetermined $CO_2$/capacity relation threshold, the battery may still be charged even if $CO_2$ is present. Therefore rechargeability of the battery and the battery lifetime can be optimized.

Alternatively, the increase rate of $CO_2$ concentration may be a relation between the increment of $CO_2$ concentration during a predetermined time interval and the predetermined time interval.

It has been found that such a relation is a reliable and especially simple criterion to determine whether charging may be continued or not without harming the battery or any unsafe use of the battery.

The battery may comprise at least one cell with an air cathode, a metal anode and a non-aqueous electrolyte. In some cases, depending on the thickness and porosity of the air cathode, said air cathode may comprise two different parts: a cathode and an air compartment. The control device may be further configured to determine the $CO_2$ concentration in the air cathode, in particular the $CO_2$ concentration dissolved in the air cathode. The $CO_2$, whose concentration is determined, may be in gas form. Due to the gas form of the $CO_2$, it can be reliably measured. The air cathode is typically a Gas Diffusion Electrode (GDE) which is porous. So typically the pores of the GDE are expected to be filled in with the electrolyte from the moment the battery is assembled. During the discharge the pores will be filled slowly with the discharge product $Li_2O_2$. During the charge at first typically the $Li_2O_2$ will be decomposed and the pores will start to be empty again and electrolyte might fill them again. Then the $CO_2$ which might be formed during the charge (at the same time as $O_2$ coming from $Li_2O_2$ decomposition) will be formed at the surface of the GDE typically within the pores of the GDE. If these pores are filled with the electrolyte, the $CO_2$ formed at the surface of GDE will be first dissolved in the electrolyte filling the pores of GDE. After a certain sufficient amount of $CO_2$ is formed, the $CO_2$ will typically produce bubbles created inside the pores of cathode at first which will be moving slowly inside the gas compartment as a gas.

The control device may be further configured to determine the $CO_2$ concentration in the electrolyte of the battery. The $CO_2$, whose concentration is determined, may be $CO_2$ dissolved inside the electrolyte (gas is soluble to certain extend in some solution-here the solvent of the electrolyte). The $CO_2$ dissolved in the solvent/electrolyte could be measured by some $CO_2$ sensor. When the solubility reaches a certain maximum, $CO_2$ gas will be formed and create bubbles escaping from the electrolyte through the cathode and the gas compartment then.

The battery may further comprise a gas compartment and at least one cell with an air cathode, a metal anode and a non-aqueous electrolyte. The cell may be arranged inside the gas compartment. The control device may be further configured to determine the $CO_2$ concentration in the gas compartment. Accordingly, the $CO_2$ generated in the cell and emitted into the gas compartment can be measured.

The control device may comprise a $CO_2$ sensor configured to measure the $CO_2$ concentration in the battery. The $CO_2$ sensor may be configured to be arranged in the air cathode and in particular configured to measure $CO_2$ in gas form. Additionally or alternatively the $CO_2$ sensor may be configured to be arranged in the non-aqueous electrolyte, in particular configured to measure $CO_2$ dissolved in the non-aqueous electrolyte. Finally alternatively or additionally the $CO_2$ sensor may be configured to be placed in the gas compartment, in particular to measure $CO_2$ in a gas form.

Accordingly, also several sensors may be used, in particular in different positions, as described.

The $CO_2$ sensor may be an electrochemical sensor and/or a semiconductor sensor.

In particular the $CO_2$ sensor may be a micro electrochemical system (solid electrolyte type $CO_2$ sensor), a chemical $CO_2$ sensor (for example based on polymer or hetero polysiloxane materials), a non-dispersive infrared absorption $CO_2$ sensor, and/or a gas chromatography-mass spectrometer (GC-MS). Said micro electrochemical system is usually relatively small so that it can be integrated in a chip for example. Another advantage of said system is that the analysis can be carried out for vapors/gases or dissolved species (ionic or non-ionic). Said chemical $CO_2$ sensor has a relatively low energy consumption and provides the possibility to be miniaturized to fit in microelectronics devices.

The disclosure further relates to a battery pack. The battery pack may comprise at least one non-aqueous metal air battery, and a control device as described above.

Hence, such a battery pack may comprise one or several non-aqueous metal air batteries. These batteries may also be referred to as cells. The battery pack may comprise further elements, like a charging device.

The non-aqueous metal air battery may comprise an air cathode, a metal anode and a non-aqueous electrolyte.

The air cathode may comprise Carbon, a binder and a catalyst. The metal air battery is desirably composed of a metal anode, a (non-aqueous) electrode and an air cathode, where $O_2$ is the main reactant. The air cathode may be a Gaz Diffusion Electrode (denoted GDE). For example, it might be composed typically of Carbon or any other conductive materials (gold, nickel . . . ), a binder and sometimes a catalyst. The catalyst may be in a solid form and contained in the air cathode. The catalyst may also be a soluble catalyst which is dissolved in certain ratio in the electrolyte and acts as a redox mediator (e.g. Tetratiafulvalene (TTF) or Iodine). In both cases, it is expected from the catalyst that it will facilitate the decomposition of the ideal discharge product being typically $Li_2O_2$. This $Li_2O_2$ is supposed to be decomposed during the charge to form back $Li^+$ and $O_2$.

The metal anode may comprise lithium, magnesium or calcium.

The disclosure further relates to a battery charging system. Said battery charging system may comprise at least one non-aqueous metal air battery, a battery management system (BMS), and a control device as described above. Said BMS may be connected to the grid or the electric motor or a supercaps or another battery or Fuel Cell which might provide electricity to charge the battery.

According to a further aspect the disclosure relates to a vehicle comprising an electric motor and a battery pack, as described above.

Alternatively the vehicle may comprise an electric motor, at least one non-aqueous metal air battery, and in addition a control device, as described above.

Further, the control device may also be part of a stationary system. Such a stationary system may comprise an electric motor, at least one non-aqueous metal air battery, and in addition a control device, as described above.

Moreover the disclosure relates to a method of controlling charging of a non-aqueous metal air battery. The method comprises the steps of:

determining a $CO_2$ concentration and an increase rate of $CO_2$ concentration in the battery during charging, charging the battery in case both the $CO_2$ concentration before starting charging exceeds a predetermined $CO_2$ threshold and the increase rate of the $CO_2$ concentration during charging is below a predetermined threshold value, and stopping charging when the increase rate exceeds the predetermined threshold value.

Charging may be started, in case the $CO_2$ concentration in the battery before starting charging does not exceed the predetermined $CO_2$ threshold. In this case, charging may be stopped when the $CO_2$ concentration in the battery during charging increases such that it exceeds the predetermined $CO_2$ threshold.

The increase rate of $CO_2$ concentration may be a $CO_2$/capacity relation, the $CO_2$/capacity relation may be in particular a relation between the increment of $CO_2$ concentration during a predetermined time interval and the increment of capacity of the battery during the predetermined time interval.

Alternatively, the increase rate of $CO_2$ concentration may be a relation between the increment of $CO_2$ concentration during a predetermined time interval and the predetermined time interval.

The battery may comprise at least one cell with an air cathode, a metal anode and a non-aqueous electrolyte.

The $CO_2$ concentration may be determined in the air cathode, in particular the $CO_2$ concentration dissolved in the air cathode.

The $CO_2$ concentration may be determined in the electrolyte of the battery, in particular dissolved in the non-aqueous electrolyte.

The battery may further comprise a gas compartment and at least one cell with an air cathode, a metal anode and a non-aqueous electrolyte. The cell may be arranged inside the gas compartment. The $CO_2$ concentration in the gas compartment may be determined.

The accompanying drawings, which are incorporated in and constitute a part of this specification, illustrate embodiments of the disclosure and together with the description, serve to explain the principles thereof.

DESCRIPTION OF THE EMBODIMENTS

Reference will now be made in detail to exemplary embodiments of the disclosure, examples of which are illustrated in the accompanying drawings. Wherever possible, the same reference numbers will be used throughout the drawings to refer to the same or like parts.

Figure 1:
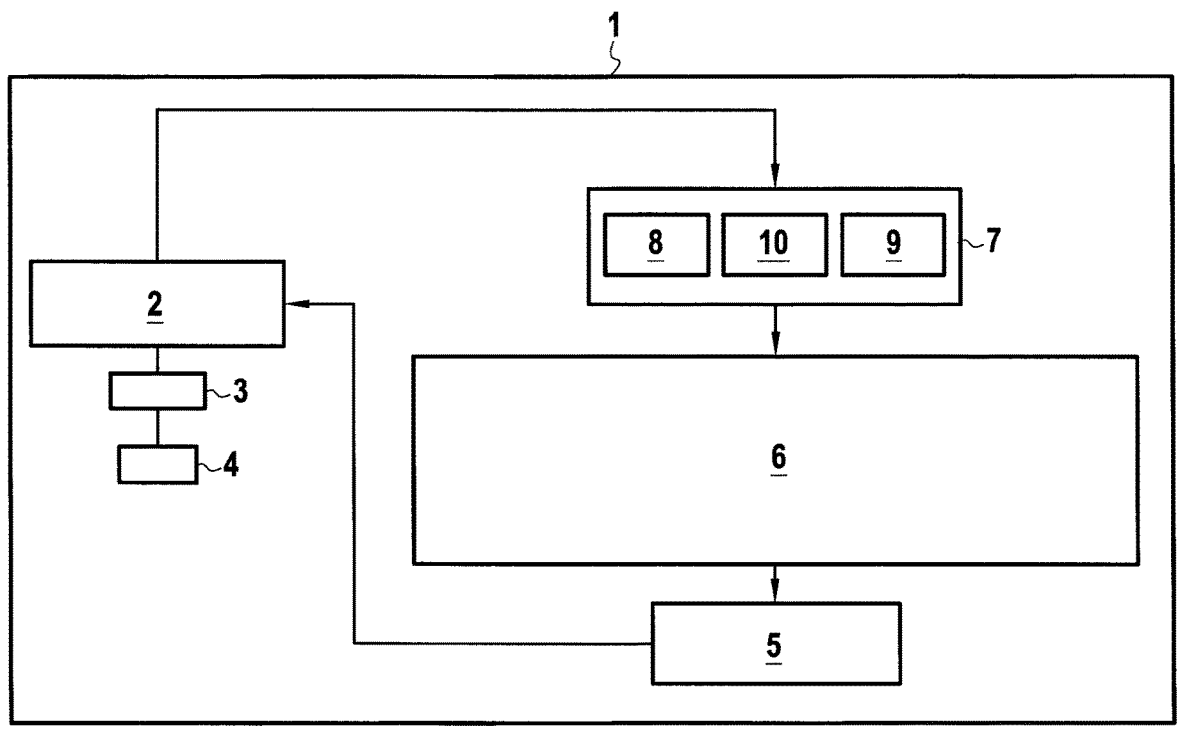
FIG. 1 shows a schematic representation of a vehicle or a stationary system comprising a control device according to an embodiment of the present disclosure.

FIG. 1 shows a schematic representation of a vehicle or a stationary system 1 comprising a control device 6 according to an embodiment of the present disclosure. In the following a vehicle 1 is described, however a stationary system comprises corresponding elements unless indicated in the to following description. The vehicle 1 may be a hybrid vehicle or an electric vehicle (i.e. a purely electrically driven vehicle). The vehicle 1 comprises at least one electric motor 4, which is powered by a battery or battery pack 2, preferably via an inverter 3. In case of a stationary system an electric distribution board 3 is desirably used instead or in addition to the inverter.

If the vehicle 1 is a hybrid vehicle, it further includes an internal combustion engine. The battery 2 is a metal air battery, in particular a non-aqueous metal air battery. The battery 2 comprises at least one cell which is preferably arranged in a gas compartment. Said gas compartment is desirably configured such that gas provided to the cell (e.g. $O_2$) and gases emitted by the cell (e.g. $O_2$, and possibly $CO_2$) can be controlled.

The battery 2 is connected to a battery management system (BMS) 5 which is configured to charge the battery 2. For this purpose the battery management system 5 may comprise an electric control circuit, as e.g. a power electronics circuit. The battery management system may further comprise or be connected to a connector for external charging by an external power source. The connector may be e.g. a plug or a wireless connector system. In case the vehicle is a hybrid vehicle, the battery management system may further be connected to the electrical generator of the internal combustion engine of the vehicle. Consequently, the battery 2 may be charged, when the internal combustion engine is operating and/or when the vehicle is connected to an external power source. Furthermore the battery 2 may be discharged, in order to operate the vehicle 1, in particular the electric motor 4. The battery 2 may further be discharged in a battery treatment and/or recovery procedure.

In order to control charging and desirably also discharging the vehicle 1 is provided with the control device 6 and one or several sensors 7. For this purpose the control device 6 monitors the battery 2 via the sensors 7 and controls the battery management system 5. The control device 6 and/or the sensors 7 may also be comprised in the battery 2. The control device may be an electronic control circuit (ECU). It may also comprise a data storage. It is also possible that the vehicle comprises a smart battery charging system with a smart battery and a smart charging device. In other words, both the battery and the vehicle may comprise each an ECU which operate together and form together the control device according to the disclosure. Furthermore the control device 6 may be part of a battery charging system. Accordingly said system comprises at least one non-aqueous metal air battery 2, a battery management system (BMS) 5, a control device 6, and desirably also the sensors 7.

The control device 6 may comprise an application specific integrated circuit (ASIC), an electronic circuit, a processor (shared, dedicated, or group), a combinational logic circuit, a memory that executes one or more software programs, and/or other suitable components that provide the described functionality of the control device 6.

As it will be explained in more detail in the following, the sensors 7 comprise in particular at least one $CO_2$ sensor 8 of a first type, at least one $CO_2$ sensor 9 of a second type, and/or at least one $CO_2$ sensor 10 of a third type.

Moreover the sensors 7 may comprise one or more temperature sensors for measuring the temperature of the battery 2, at least one current sensor (Amp sensor), in particular for measuring the state of charge of the battery 2, and at least one further voltage sensor for measuring the voltage of the battery 2. The current sensor desirably measures the current flowing into the battery during charging. The current sensor is desirably configured to measure the increase rate of capacity $\Delta Ah_x$ of the battery 2 during charging, i.e. in particular in unit A.

In case of use in a metal air battery, where air or dried air is fed to the battery pack, the sensor(s) 7 are desirably de-activated during discharge, since air will be fed to the battery and contain $CO_2$.

In case of use in a metal air battery, where air is fed to the battery via a selective membrane retaining $CO_2$ outside of the battery, the $CO_2$ sensor(s) does not need to be de-activated during discharge but may be de-activated. Correspondingly, in case of use in Metal-$O_2$ configuration where $O_2$ is fed to the battery via a tank for example or another system, the $CO_2$ sensor(s) does not need to be de-activated during discharge but may be de-activated.

Figures 2A, 2B:
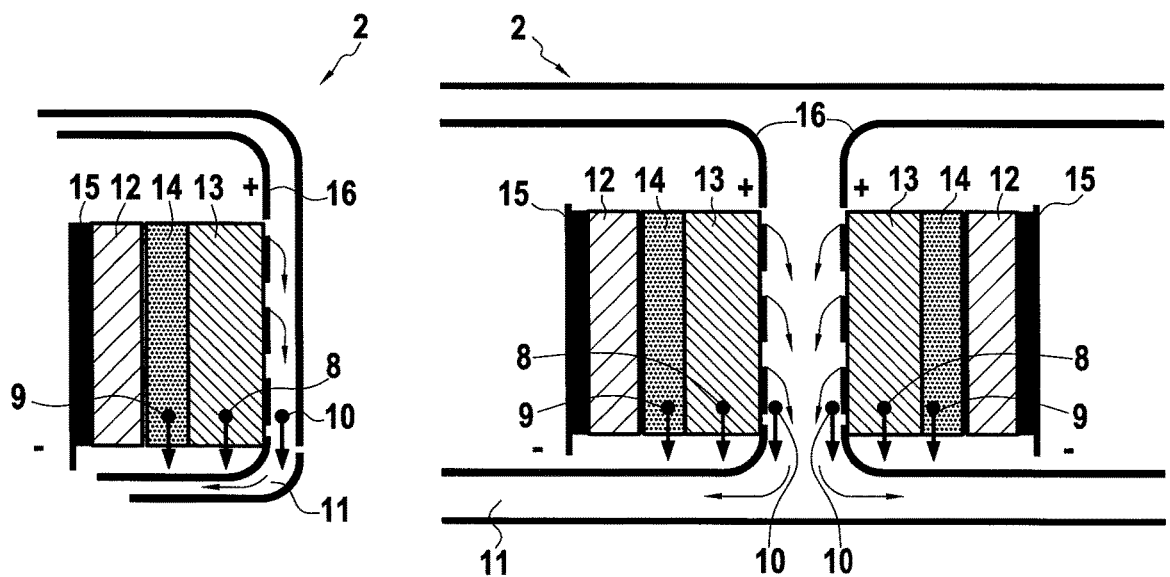
FIG. 2a shows a schematic representation of a metal air battery with a cell inside a gas compartment.
FIG. 2b shows a schematic representation of a metal air battery with several cells sharing the same gas compartment.

FIG. 2a shows a schematic representation of a metal air battery 2 with a cell inside a gas compartment 11. The gas compartment 11 is configured to encase one cell. Hence, in case the battery 2 comprises several cells, each of said cell has its own gas compartment 11. The cell is composed mainly of a metal anode 12, a (desirably non-aqueous) electrolyte (and/or separator) 14 and an air cathode 13. The electrolyte 14 is desirably placed between the anode 12 and the cathode 13. Further, the anode 12 and the cathode 13 comprise respectively an anode collector 15 and a cathode collector 16 on their outer surfaces. The anode collector 15 and the cathode collector 16 are connected to an electrical circuit.

The anode 12 desirably comprises or consists of Lithium (Li). In the cathode 13, $O_2$ is desirably the main reactant. The air cathode may be a Gas Diffusion Electrode (denoted GDE). For example, it might be composed typically of Carbon or any other conductive materials (gold, nickel . . . ), a binder and sometimes a catalyst. The catalyst may be in a solid form and contained in the air cathode. The catalyst may also be a soluble catalyst which is dissolved in certain ratio in the electrolyte and acts as a redox mediator (e.g. Tetratiafulvalene (TTF) or Iodine). In both cases, it is expected from the catalyst that they will facilitate the decomposition of the ideal discharge product being typically $Li_2O_2$. This $Li_2O_2$ is supposed to be decomposed during the charge to form back $Li^+$ and $O_2$. The cathode is usually a support for $O_2$ reaction.

A $CO_2$ sensor 8 of the first type may be positioned and configured such that it measures $CO_2$ in the air cathode 13, in particular the $CO_2$ concentration dissolved in the air cathode. In such case the $CO_2$ is detected in its gas form.

Alternatively or additionally a $CO_2$ sensor 9 of the second type may be placed in the electrolyte/separator 14. In such case the sensor 9 is positioned and configured such that it measures $CO_2$ dissolved in the electrolyte.

Alternatively or additionally a $CO_2$ sensor 10 of the third type may be placed in the electrolyte/separator 14. In such case the sensor 10 is positioned and configured such that it measures $CO_2$ dissolved in the electrolyte. Gas is usually soluble to a certain extend in some solution, i.e. the solvent of the electrolyte. When the solubility reaches a certain maximum, $CO_2$ gas will be formed and create bubbles escaping from the electrolyte through the cathode and the gas compartment 11 then.

FIG. 2b shows a schematic representation of a metal air battery 2 with several cells sharing the same gas compartment 11. The cells are arranged inside said gas compartment. In FIG. 2b two cells are shown, however, also a higher number of cells my be comprised by the battery. As it is shown the cell and the sensors 8 to 10 correspond to those of FIG. 2a. In case of a non-aqueous metal air battery using 2-compartment cells, where two different types of electrolytes will be used at anode side and cathode side, the $CO_2$ sensor of the second type is desirably positioned and configured such that it measures $CO_2$ in the compartment side of the cathode. Accordingly, only one of the sensors 10 shown in FIG. 2b may be used in the whole battery.

Generally, the ideal reaction should be as follows: During discharge $O_2$ is consumed to form ideal product $Li_2O_x$:2 Li+x/2 $O_2 \rightarrow Li_2O_x$. This reaction is actually taking place in several steps in which the first one is related to the formation of $O_2^-$ radicals as follows: $O_2+e^- \rightarrow O_2^-$. During charge $O_2$ is released: $Li_2O_x \rightarrow 2$ Li+x/2 $O_2$.

Nevertheless, during electrochemical processes of the battery, it can happen that some side reactions take place (for example $O_2^-$ radicals react with the solvent molecules of the electrolyte and lead to the formation of side reactions products such as Lithium Carbonate ($Li_2CO_3$), Li formate, Lithium acetate, etc.). As a result, during the charging process it can happen that $CO_2$ gas is released. In such case, bad re-chargeability of the battery occurs and poor capacity retention is observed.

Accordingly, during charging of the battery as described above, it is possible that an unwanted product such as $CO_2$ gas is evolved instead of or in addition to the expected $O_2$ gas. This $CO_2$ is detrimental for the battery since it contributes to the degradation of the battery.

Furthermore, this $CO_2$ is an indication that the battery is overcharging and usually is linked with a strong increase of voltage which is an indication of an unsafe use of the battery.

As an example, for a small scale Li—$O_2$ battery made with a cathode of approximately 1 mg carbon nanotubes (CNT), using 150 μL of electrolyte, having a capacity of >1000 mAh/-gCNT, during $1^{st}$ discharge in total 7000 nmol of $O_2$ can be consumed while <1000 nmol of $CO_2$ should be released. The gas production rate of $O_2$ for such battery will be in the range of <100 nmol $O_2$/min, or <80 nmol $O_2$/min, or <60 nmol $O_2$/min. In the meantime, the gas production rate of $CO_2$ for such battery will be in the range of <25 nmol $CO_2$/min, or <20 nmol $CO_2$/min or <15 nmol $CO_2$/min or preferentially even below. It is clear that if the cathode size is greater, the amount of $O_2$ and $CO_2$ possibly produced will be different and then the sensor(s) specificities and accuracies will need to be adapted accordingly after experimental determination. Hence, the sensors 7 should be configured such that they detect $CO_2$ gas in such dimensions. Generally, the sensors 7 should be configured such that they detect $CO_2$ as gas and/or as $CO_2$ dissolved in a non-aqueous media, or they should detect $CO_2$ in presence of other gas ($O_2$ especially). The sensors should be as small as possible (especially for automotive applications where volume matters). The detected level of $CO_2$ should be expressed in ppm (ppm or % volume). The range should depend on the capacity of the battery.

Figure 3A:
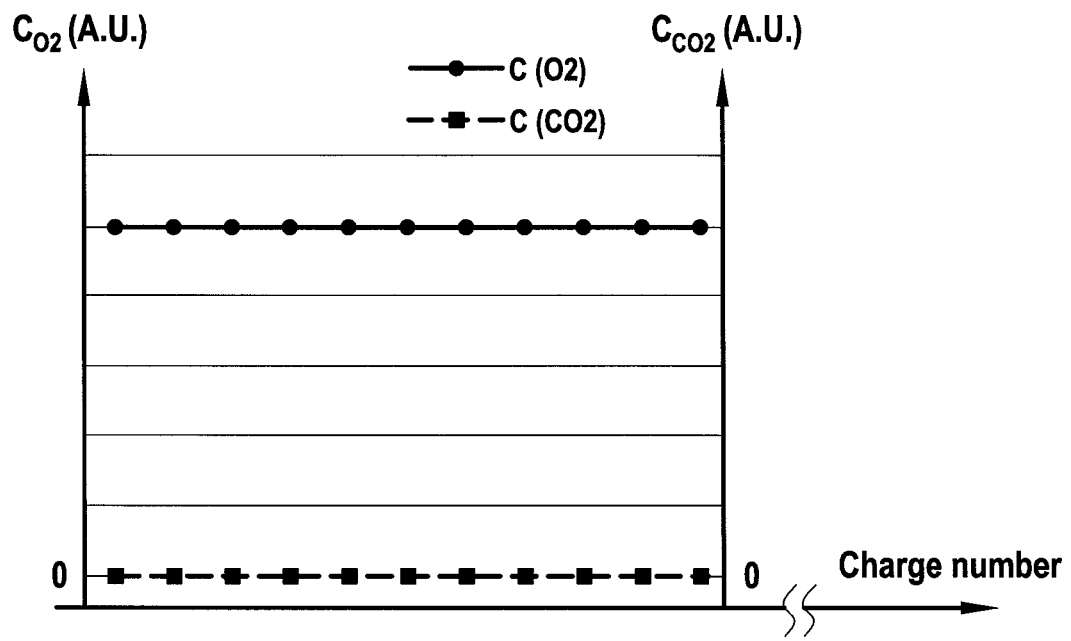
FIGS. 3a and 3b show exemplary and schematic diagrams of the ideal and the real case of $O_2$ and $CO_2$ production during the lifetime of the battery.
Figure 3B:
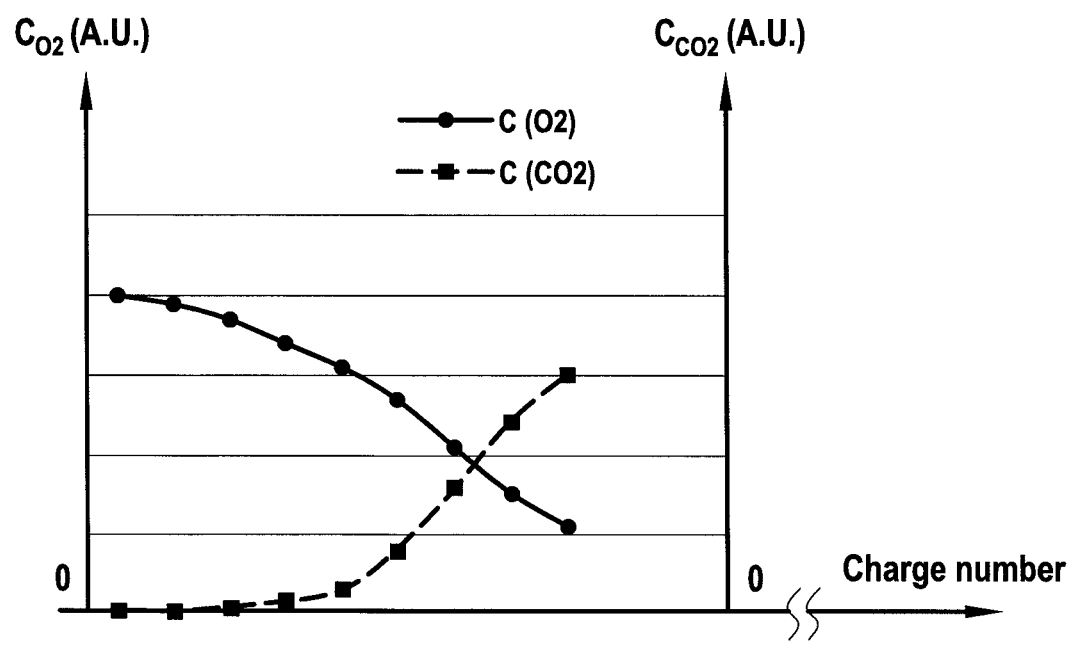

FIGS. 3a and 3b show exemplary and schematic diagrams of the ideal and the real case of $O_2$ and $CO_2$ production during the lifetime of the battery. FIG. 3a shows an ideal case, where no $CO_2$ is produced during lifetime of the battery, i.e. the $CO_2$ concentration in the battery during the charge cycles of the battery life is constantly zero. Accordingly, the concentration of the necessary reactant $O_2$ is constantly high during the lifetime of the battery. However in a real case as shown in FIG. 3b, the concentration of $CO_2$ increases during lifetime of the battery, i.e. during the charge cycles of the battery life. At the same time the concentration of $O_2$ decreases during the lifetime of the battery.

Figure 4:
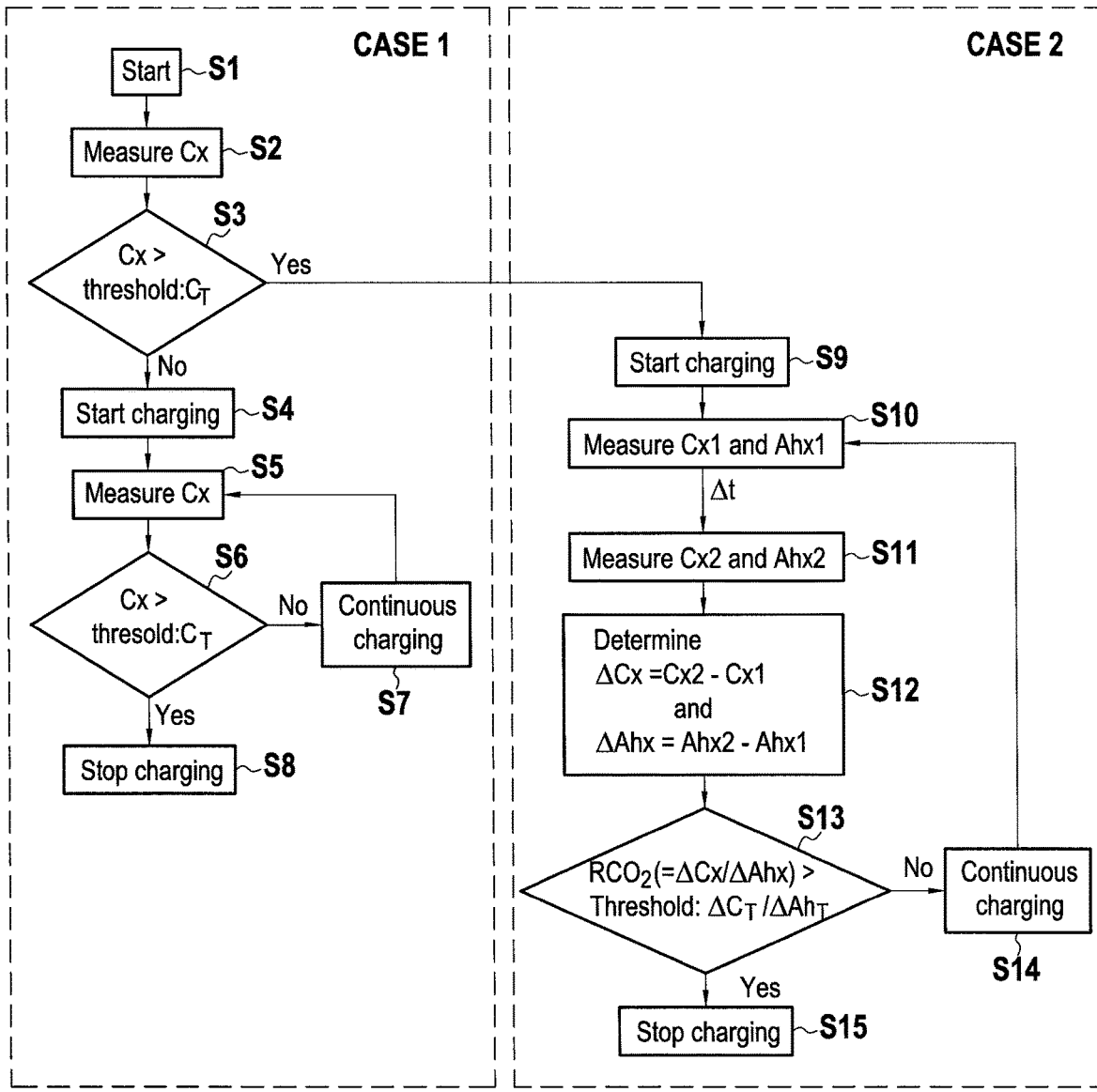
FIG. 4 shows a flow chart of the charging control procedure according to an embodiment of the present disclosure.

FIG. 4 shows a flow chart of the charging control procedure according to an embodiment of the present disclosure. The procedure may be carried out by the control device 6.

In step S1 the procedure is started. The start may be triggered by a determination of the control device that charging of the battery is necessary (e.g. due to a low state of charge) and/or by the fact that charging becomes possible (e.g. due to operation of the internal combustion engine or due to a connection to an external electrical power source).

In step S2 the concentration of $CO_2$ is measured. Based on this measurement result it is determined in step S3 whether the measured $CO_2$ concentration exceeds a predetermined $CO_2$ concentration threshold. In case it does not, charging is started in step S4 and the conventional charging control procedure (i.e. case 1) is carried out.

In step S5 the $CO_2$ concentration is measured again, however now during charging. Based on this measurement result it is determined in step S6 whether the measured $CO_2$ concentration exceeds the predetermined $CO_2$ concentration threshold $C_T$. In case it does not, charging is continued in step S7 and it is returned to step S5. Hence, as long as the measured $CO_2$ concentration does not exceed the predetermined $CO_2$ concentration and the battery is not yet fully charged, the loop S5 to S7 is continuously run, i.e. the $CO_2$ concentration is continuously monitored during charging. The loop may be repeated every 5 or 10 seconds or once per minute.

In case the measured $CO_2$ concentration exceeds the predetermined $CO_2$ concentration in step S6, or in case the battery is fully charged, charging is stopped in step S8.

The predetermined $CO_2$ concentration threshold $C_T$ is the threshold concentration of $CO_2$ which is desirably determined experimentally in advance depending on the battery specifications (type, size, volume, packaging, shape, etc.) and applications (automotive, stationary, etc.).

In case it is determined in step S3 that before starting charging the measured $CO_2$ concentration exceeds the predetermined $CO_2$ concentration threshold, charging is started in step S9 and the charging control procedure according to case 2 is carried out. In this procedure charging is controlled based on the determined increase rate of $CO_2$ concentration $\Delta C_x$.

In step S10 the $CO_2$ concentration $C_{x1}$ and the capacity of the battery $Ah_{x1}$ are measured at a first time point.

Subsequently, in step S11 the $CO_2$ concentration $C_{x2}$ and the capacity of the battery $Ah_{x2}$ are measured at a second time point, i.e. after a predetermined time interval $\Delta t$ of e.g. 1, 5 or 10 minutes.

In step S12 the increment of $CO_2$ concentration $\Delta C_x$ is determined, i.e. $\Delta C_x = C_{x2} - C_{x1}$. Furthermore the increment of capacity $\Delta Ah_x$ is determined or measured, i.e. $\Delta Ah_x = Ah_{x2} - Ah_{x1}$.

In step S13, the relation of $\Delta C_x / \Delta Ah_x$ is determined which provides the increase rate $RCO_2$ of $CO_2$ concentration. Furthermore it is determined, whether the relation $\Delta C_x / \Delta Ah_x$ exceeds a predetermined relation threshold $\Delta C_T / \Delta Ah_T$.

In case it does not, charging is continued in step S14 and it is returned to step S10. Hence, as long as the measured relation $\Delta C_x / \Delta Ah_x$ does not exceed the predetermined relation threshold $\Delta C_T / \Delta Ah_T$ and the battery is not yet fully charged, the loop S10 to S14 is continuously run, i.e. the $CO_2$ concentration increase rate in view of the capacity increase rate is continuously monitored during charging. The loop may be repeated every 5 or 10 seconds or once per minute.

In case the relation $\Delta C_x / \Delta Ah_x$ determined in step S13 exceeds the predetermined relation threshold $\Delta C_T / \Delta Ah_T$ or in case the battery is fully charged, charging is stopped in step S15.

The predetermined relation threshold $\Delta C_T / \Delta Ah_T$ is the threshold rate of formation of $CO_2$ which is desirably determined in advance depending on the battery specifications (type, size, volume, packaging, shape, etc.) and applications (automotive, stationary, etc.).

According to an alternative embodiment the same procedure is applied as described above in context of FIG. 4 but with the following differences in steps S10 to S13:

In steps S10 and S11 the $CO_2$ concentrations $C_{x1}$ and $C_{x2}$ are measured at a first and a second time point but not necessarily the capacity of the battery $Ah_{x1}$ and $Ah_{x2}$.

In step S12 the increment of $CO_2$ concentration $\Delta C_x$ is determined, i.e. $\Delta C_x = C_{x2} - C_{x1}$.

In step S13, the increase rate $RCO_2$ of $CO_2$ concentration is determined as a relation $\Delta C_x/\Delta t$. Hence, in this alternative embodiment the increase rate of $CO_2$ concentration $\Delta C_x$ per time interval $\Delta t$ is determined. Furthermore it is determined, whether the relation $\Delta C_x/\Delta t$ exceeds a predetermined relation threshold $\Delta C_T/\Delta t$.

It should be noted that in the charging control procedure according to case 2 $CO_2$ will be released and will deteriorate the battery but in a moderate way. However, if only a moderate amount of $CO_2$ is given to the battery, the battery can still work even if it deteriorates a bit. Only if a too strong amount of $CO_2$ is given to the battery, the battery might become completely inoperable.

According to a first example, in case the battery will use air as a source of $O_2$, $CO_2$ present in the air will enter the battery during the discharge process. In such case, during the charge it is possible that the sensor(s) will detect $CO_2$ present in the battery. But even in this case, the battery should be able to be charged. The charging control procedure according to case 2 will then apply to charge the battery.

According to a second example, in case a Li-Air ($O_2$) battery uses an electrolyte like Propylene carbonate or other carbonates or a mixture of electrolyte containing carbonates, etc., $Li_2CO_3$ will be (partially) the discharge product (instead of $Li_2O_2$). When $Li_2CO_3$ decomposes, it forms $CO_2$ in majority (less/no $O_2$). However, charging can still be controlled with the charging control procedure according to case 2.

According to a third example, in case the Li-Air ($O_2$) battery uses a more suitable electrolyte (e.g. DME (Dimethoxyethane, also known as glyme, monoglyme, dimethyl glycol, ethylene glycol dimethyl ether) but does not contain a catalyst, $Li_2O_2$ is the main discharge product. But still it may be difficult to decompose $Li_2O_2$ without a catalyst in order to form $O_2$. Then the potential of the battery will raise and there may be a competition between the $Li_2O_2$ decomposition to form $O_2$ and the electrolyte decomposition to form $CO_2$. Then it is possible that $C_x > C_T$. However, charging can still be controlled with the charging control procedure according to case 2.

Figure 5A:
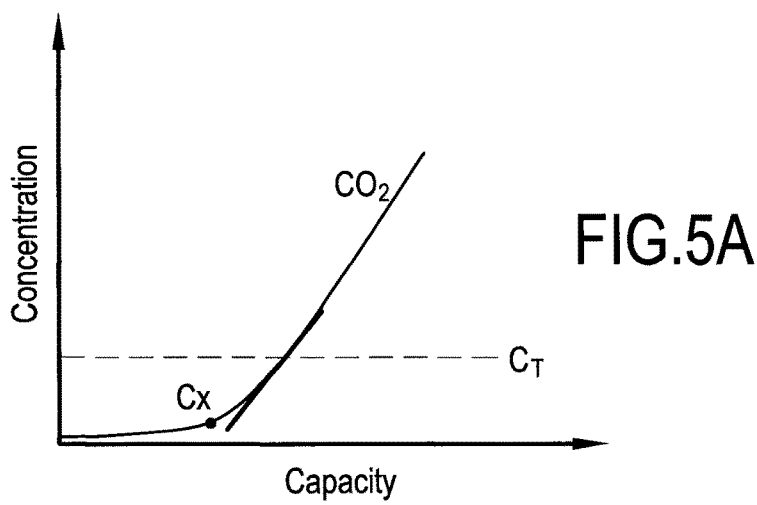
FIG. 5a to 5c show exemplary and schematic diagrams of different $CO_2$ concentrations and increase rates in the battery during one charging cycle.
Figure 5B:
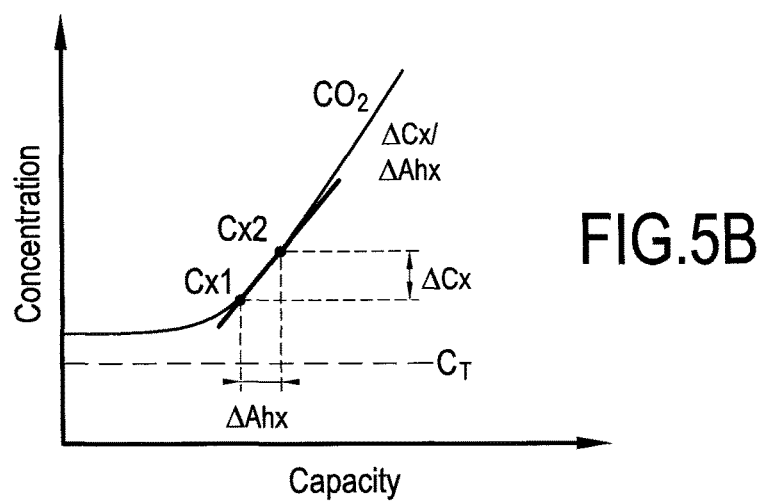
Figure 5C:
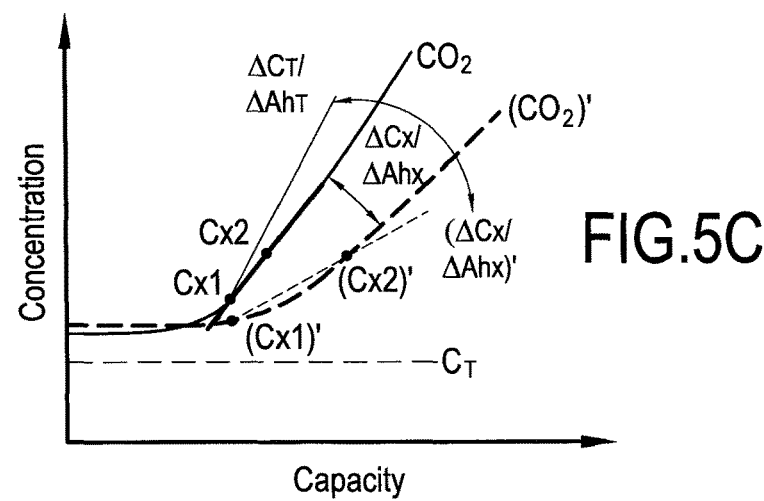

FIG. 5a to 5c show exemplary and schematic diagrams of different $CO_2$ concentrations and increase rates in the battery during charging (i.e. one charging cycle). The diagrams show the development of the $CO_2$ concentration $C_x$ versus the development of the capacity $Ah_x$ during charging, i.e. during a charging cycle. As can be seen in FIG. 5a to 5c, the $CO_2$ concentration may generally increase (with an increasing capacity) during charging according to a charging curve form, as $CO_2$ may be produced during the charging.

FIG. 5a shows a first scenario where the $CO_2$ concentration $C_x$ before starting charging is below a predetermined $CO_2$ threshold $C_T$. Accordingly, the charging control procedure according to case 1 of FIG. 4 is carried out.

FIG. 5b shows a second scenario where the $CO_2$ concentration $C_x$ before starting charging already exceeds a predetermined $CO_2$ threshold $C_T$. Accordingly, the charging control procedure according to case 2 of FIG. 4 is carried out. In other words, during charging the relation $\Delta X_x/\Delta Ah_x$ is determined.

FIG. 5c shows the second scenario of FIG. 5b and a third scenario which generally corresponds to the second scenario of FIG. 5b. In both scenarios, the $CO_2$ concentration $C_x$ before starting charging already exceeds a predetermined $CO_2$ threshold $C_T$. Accordingly, the charging control procedure according to case 2 of FIG. 4 is carried out. During charging the relation $\Delta C_x/\Delta Ah_x$ is determined and compared to a predetermined relation threshold $\Delta C_T/\Delta Ah_T$ (indicated as thin continuous line). Accordingly, any relation $\Delta C_x/\Delta Ah_x$ having a smaller slope than the predetermined relation threshold is allowed. In the present scenario, the battery of the second scenario has a greater relation $\Delta C_x/\Delta Ah_x$ (bold continuous line) and the battery of the third scenario a smaller relation $(\Delta C_x/\Delta Ah_x)'$ (thin dashed line). However, in both examples the relations $\Delta C_x/\Delta Ah_x$ and $(\Delta C_x/\Delta Ah_x)'$ do not exceed the predetermined relation threshold $\Delta C_T/\Delta Ah_T$ and hence charging is carried out until the battery is fully charged.

Throughout the disclosure, including the claims, the term "comprising a" should be understood as being synonymous with "comprising at least one" unless otherwise stated. In addition, any range set forth in the description, including the claims should be understood as including its end value(s) unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances.

Where any standards of national, international, or other standards body are referenced (e.g., ISO, etc.), such references are intended to refer to the standard as defined by the national or international standards body as of the priority date of the present specification. Any subsequent substantive changes to such standards are not intended to modify the scope and/or definitions of the present disclosure and/or claims.

Although the present disclosure herein has been described with, reference to particular embodiments, it is to be understood that these embodiments are merely illustrative of the principles and applications of the present disclosure.

It is intended that the specification and examples be considered as exemplary only, with a true scope of the disclosure being indicated by the following claims.

The invention claimed is:

1. A control device for controlling charging of a non-aqueous metal air battery, the control device being configured to:
   determine a $CO_2$ concentration ($C_x$) and an increase rate ($RCO_2$) of $CO_2$ concentration in the battery,
   charge the battery in case both the $CO_2$ concentration (CO before starting charging exceeds a predetermined $CO_2$ threshold ($C_T$) and the increase rate of the $CO_2$ concentration ($RCO_2$) during charging is below a predetermined threshold value ($\Delta C_T/\Delta Ah_T$, $\Delta C_T/\Delta t$), and
   stop charging when the increase rate ($RCO_2$) exceeds the predetermined threshold value ($\Delta C_T/\Delta Ah_T$, $\Delta C_T/\Delta t$),
   wherein the battery comprises a gas compartment, at least one cell with an air cathode, a metal anode, and a non-aqueous electrolyte, the gas compartment is configured such that a reactant provided to the cell is controlled, the control device is configured to control feeding of the reactant to the battery, and the control device is configured to determine the $CO_2$ concentration ($C_x$) in at least one of the air cathode and the non-aqueous electrolyte, and wherein the control device includes a $CO_2$ sensor configured to measure the $CO_2$ concentration ($C_x$) in the battery, the $CO_2$ sensor is configured to be arranged in at least one of the air cathode, the non-aqueous electrolyte, and the gas compartment, and the $CO_2$ sensor is deactivated during discharge of the battery.

2. The control device according to claim 1, further configured to:

charge the battery, in case the $CO_2$ concentration ($C_x$) in the battery before starting charging does not exceed the predetermined $CO_2$ threshold ($C_T$), and in this case, stop charging when the $CO_2$ concentration in the battery during charging increases such that it exceeds the predetermined $CO_2$ threshold ($C_T$).

3. The control device according to claim 1, wherein the increase rate ($RCO_2$) of $CO_2$ concentration is a $CO_2$/capacity relation ($\Delta C_x/\Delta Ah_x$), the $CO_2$/capacity relation ($\Delta C_x/\Delta Ah_x$) being a relation between the increment of $CO_2$ concentration ($\Delta C_x$) during a predetermined time interval ($\Delta t$) and the increment of capacity ($\Delta Ah_x$) of the battery during the predetermined time interval ($\Delta t$).

4. The control device according to claim 1, wherein the increase rate ($RCO_2$) of $CO_2$ concentration is a relation ($\Delta C_x/\Delta t$) between the increment of $CO_2$ concentration ($\Delta C_x$) during a predetermined time interval ($\Delta t$) and the predetermined time interval ($\Delta t$).

5. The control device according to claim 1, the battery additionally comprising a metal anode and a non-aqueous electrolyte, wherein the cell is arranged inside the gas compartment, and the control device is further configured to determine the $CO_2$ concentration ($C_X$) in the gas compartment.

6. The control device according to claim 1, wherein the $CO_2$ sensor is an electrochemical sensor and/or a semiconductor sensor.

7. A battery pack comprising:

at least one non-aqueous metal air battery, and a control device according to claim 1.

8. The battery pack according to claim 7, the non-aqueous metal air battery comprising at least one cell with an air cathode, a metal anode and a non-aqueous electrolyte.

9. A vehicle comprising:

an electric motor, and a battery pack according to claim 7.

10. A battery charging system comprising:

at least one non-aqueous metal air battery, a battery management system for the battery, and a control device according to claim 1.

11. A vehicle comprising:

an electric motor, at least one non-aqueous metal air battery, and a control device according to claim 1.

12. The control device according to claim 1, wherein the reactant is $O_2$.

13. The control device according to claim 1, wherein the reactant is fed to the battery during discharge of the battery.

14. A method of controlling charging of a non-aqueous metal air battery, the battery comprising a gas compartment, at least one cell with an air cathode, a metal anode, and a non-aqueous electrolyte, the gas compartment being configured such that a reactant provided to the cell is controlled, the method comprising the steps of:

feeding the reactant to the battery, providing a $CO_2$ sensor configured to measure a $CO_2$ concentration ($C_x$) in the battery, arranging the $CO_2$ sensor in at least one of the air cathode, the non-aqueous electrolyte, and the gas compartment, the $CO_2$ sensor being deactivated during discharge of the battery, determining the $CO_2$ concentration ($C_x$) in at least one of the air cathode and the non-aqueous electrolyte, determining an increase rate ($RCO_2$) of $CO_2$ concentration in the battery, charging the battery in case both the $CO_2$ concentration ($C_x$) before starting charging exceeds a predetermined $CO_2$ threshold ($C_T$) and the increase rate of the $CO_2$ concentration ($RCO_2$) during charging is below a predetermined threshold value, and stopping charging when the increase rate ($RCO_2$) exceeds the predetermined threshold value ($\Delta C_T/\Delta Ah_T$, $\Delta C_T/\Delta t$).

15. The method according to claim 14, further comprising the steps of:

charging the battery, in case the $CO_2$ concentration ($C_x$) in the battery before starting charging does not exceed the predetermined $CO_2$ threshold ($C_T$), and in this case, stopping charging when the $CO_2$ concentration in the battery during charging increases such that it exceeds the predetermined $CO_2$ threshold ($C_T$).

16. The method according to claim 14, wherein the increase rate ($RCO_2$) of $CO_2$ concentration is a $CO_2$/capacity relation ($\Delta C_x/\Delta Ah_x$), the $CO_2$/capacity relation ($\Delta C_x/\Delta Ah_x$) being a relation between the increment of $CO_2$ concentration ($\Delta C_x$) during a predetermined time interval ($\Delta t$) and the increment of capacity ($\Delta Ah_x$) of the battery during the predetermined time interval ($\Delta t$).

17. The method according to claim 14, wherein the increase rate ($RCO_2$) of $CO_2$ concentration is a relation ($\Delta C_X/\Delta t$) between the increment of $CO_2$ concentration ($\Delta C_X$) during a predetermined time interval ($\Delta t$) and the predetermined time interval ($\Delta t$).

18. The method according to claim 14, wherein the $CO_2$ concentration ($C_X$) is determined in the gas compartment.

19. A control device for controlling charging of a non-aqueous metal air battery, the control device being configured to:

determine a $CO_2$ concentration (CO and an increase rate ($RCO_2$) of $CO_2$ concentration in the battery, charge the battery in case both the $CO_2$ concentration ($C_x$) before starting charging exceeds a predetermined $CO_2$ threshold ($C_T$) and the increase rate of the $CO_2$ concentration ($RCO_2$) during charging is below a predetermined threshold value ($\Delta C_T/\Delta Ah_T$, $\Delta C_T/\Delta t$), and stop charging when the increase rate ($RCO_2$) exceeds the predetermined threshold value ($\Delta C_T/\Delta Ah_T$, $\Delta C_T/\Delta t$), wherein the control device includes a $CO_2$ sensor configured to measure the $CO_2$ concentration ($C_x$) in the battery and the $CO_2$ sensor is deactivated during discharge of the battery.

* * * * *